(12) United States Patent
Gruber et al.

(10) Patent No.: US 10,016,253 B2
(45) Date of Patent: Jul. 10, 2018

(54) DENTAL WATER TECHNOLOGY

(71) Applicant: Mark L. Anderson, Spring Valley, WI (US)

(72) Inventors: Charles Gruber, Elmwood, WI (US); Amy Ley, River Falls, WI (US); Jim Wait, Spring Valley, WI (US)

(73) Assignee: Mark L. Anderson, Spring Valley, WI (US)

( * ) Notice: Subject to any disclaimer, the term of this patent is extended or adjusted under 35 U.S.C. 154(b) by 0 days.

(21) Appl. No.: 14/997,063

(22) Filed: Jan. 15, 2016

(65) Prior Publication Data

US 2016/0262848 A1    Sep. 15, 2016

Related U.S. Application Data

(60) Provisional application No. 62/104,141, filed on Jan. 16, 2015.

(51) Int. Cl.
*A61C 1/05*      (2006.01)
*A61C 1/00*      (2006.01)

(52) U.S. Cl.
CPC .......... *A61C 1/0084* (2013.01); *A61C 1/0061* (2013.01); *A61C 1/0076* (2013.01); *A61C 1/05* (2013.01); *A61C 1/0023* (2013.01)

(58) Field of Classification Search
CPC ... A61C 1/0007; A61C 1/0069; A61C 1/0092; A61C 1/0052; A61C 17/02; A61C 1/0084; A61C 1/0061; A61C 1/0076; A61C 1/05; A61C 1/0023; F16K 31/122; F16K 31/1221

USPC ...... 433/80, 82, 84–85, 87, 98–101; 251/63, 251/63.5, 63.6
See application file for complete search history.

(56) References Cited

U.S. PATENT DOCUMENTS

| | | | |
|---|---|---|---|
| 3,052,444 A * | 9/1962 | Kintner | F16K 31/122 137/882 |
| 3,100,001 A * | 8/1963 | Forwald | F16K 31/122 137/596.1 |
| 3,902,247 A * | 9/1975 | Fleer | A61C 1/0007 433/28 |
| 3,918,161 A | 11/1975 | Morgan et al. | |
| 4,069,587 A | 1/1978 | Peralta | |
| 4,185,385 A | 1/1980 | Simor | |
| 4,234,015 A * | 11/1980 | Kintner | F16K 11/065 137/625.18 |
| 5,309,934 A * | 5/1994 | Jaeger | F16K 1/12 137/1 |
| 5,360,338 A | 11/1994 | Waggoner | |
| 5,429,304 A * | 7/1995 | Tomita | B05B 3/1057 239/119 |

(Continued)

*Primary Examiner* — Edward Moran
*Assistant Examiner* — Drew Folgmann
(74) *Attorney, Agent, or Firm* — Skinner and Associates; Joel Skinner

(57) ABSTRACT

A heat sterizable, independent dental water supply apparatus has a hand piece control head and a water supply container removably connected to the control head. The apparatus in connectible with a dental, hand piece, an air source and a controller such as a dental foot pedal. In use, the apparatus supplies sterile irrigation water at the hand piece under the control of a dental practitioner. The apparatus is particularly useful of oral surgeons, prosthodontists and other dental specialists. Methods of making and using the apparatus are also disclosed.

11 Claims, 16 Drawing Sheets

(56) References Cited

U.S. PATENT DOCUMENTS

| | | | |
|---|---|---|---|
| 5,468,148 A * | 11/1995 | Ricks | A61C 17/02 |
| | | | 433/80 |
| 5,478,236 A | 12/1995 | Annunzio | |
| 6,364,170 B1 | 4/2002 | Anderson et al. | |
| 8,123,522 B2 | 2/2012 | Varnes | |
| 2004/0231732 A1 * | 11/2004 | Jeter | B05C 11/1026 |
| | | | 137/597 |

* cited by examiner

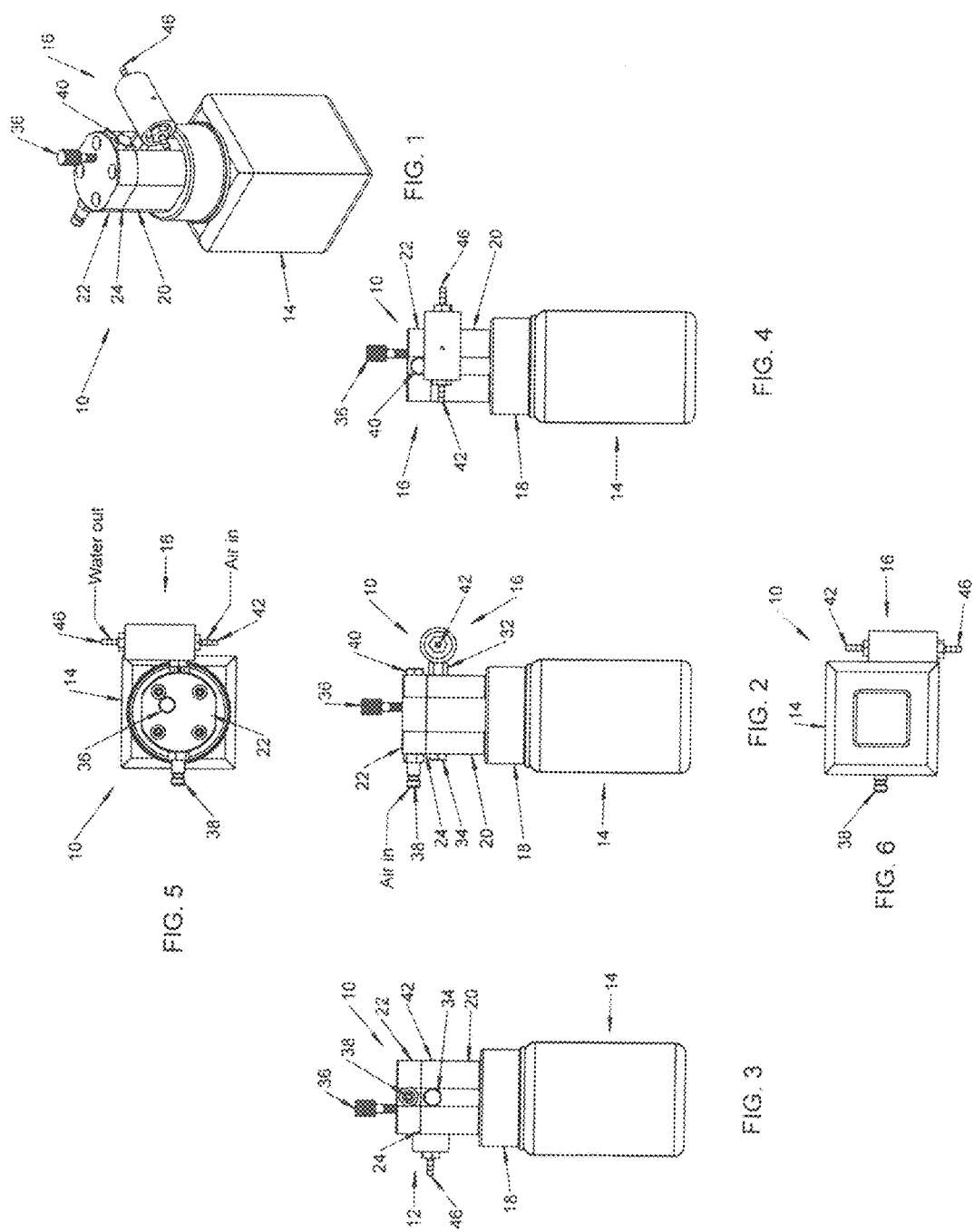

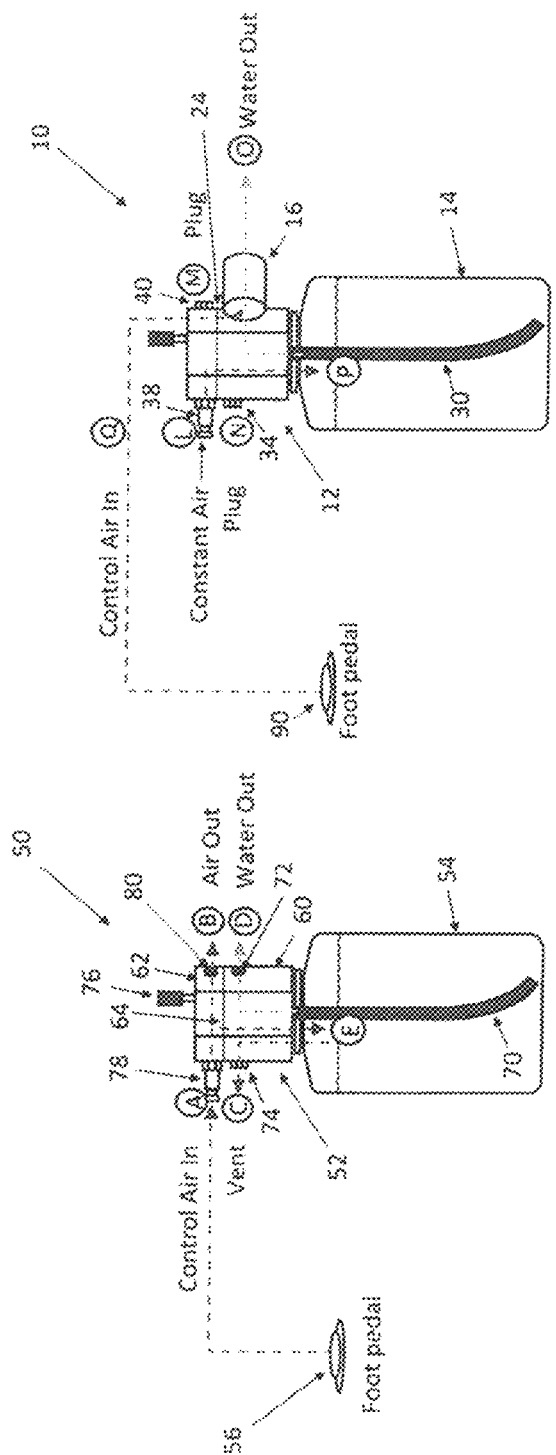

DENTAL WATER TECHNOLOGY

CROSS-REFERENCE TO RELATED APPLICATIONS, IF ANY

This application claims the benefit under 35 U.S.C. § 119(e) of U.S. Provisional Patent Application Ser. No. 62/104,141, filed Jan. 16, 2015, which is hereby incorporated by reference.

37 C.F.R. § 1.71 (e) AUTHORIZATION

A portion of the disclosure of this patent document contains material which is subject to copyright protection. The copyright owner has no objection to the fee-simile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND

1. Field

The present invention relates, generally, to dental apparatus and methods. More particularly, the invention relates to dental drills, irrigators and air supplies. Most particularly, the invention relates to a system, apparatus and methods for providing drive, coolant, and irrigation liquids in a dental hand piece. The techniques of the invention can also be used in other fields such as medical apparatus and methods.

2. Background Information

Dental hand pieces may provide means for drilling, drilling coolant, irrigation, mist air, air, and combinations thereof. A problem which can occur in apparatus is backflow of saliva, blood, bacteria or other liquids from the mouth of the patient into the reservoir which houses the coolant. Disposable or serializeable containers may aid in avoiding such transfer of contaminated material. Some microorganisms, including those found on dental hand pieces maybe resistant to chemical disinfection. Therefore, autoclave (heat and pressure) disinfection or sterilization is desirable. A complete hand piece system, including the Hand piece, Water Line and Water/Water Container, that is amenable to autoclave disinfection and use in the sterile zone is desirable. It is particularly beneficial that the entire system be operable by the user with gloves on.

Existing technology in this field is believed to have significant limitations and shortcomings.

All US patents and patent applications, and all other published documents mentioned anywhere in this application are hereby incorporated by reference in their entirety.

BRIEF SUMMARY

The present invention provides a dental air and water supply system, apparatus and methods which are practical, reliable, effective and safe, and which are believed to constitute an improvement over the background technology.

The invention provides a heat sterizable, independent dental water supply apparatus. The apparatus includes a hand piece control head and a water supply container removably connected to the control head. The apparatus in connective with a dental hand piece, an air source and a controller such as a dental foot pedal. In use, the apparatus supplies sterile irrigation water at the hand piece under the control of a dental practitioner. The apparatus is particularly useful of oral surgeons, prosthodontists and other dental specialists.

The invention also provides methods of making and using the apparatus of the invention.

The present invention is believed to involve novel elements, combined in novel ways to yield more than predictable results. The problems solved by the invention were not fully recognized in the prior art.

The aspects, features, advantages, benefits and objects of the invention will become clear to those skilled in the art by reference to the following description, claims and drawings.

BRIEF DESCRIPTION OF THE SEVERAL VIEWS OF THE DRAWING

The present invention, and the manner and process of making and using it, will be better understood by those skilled in the art by reference to the following drawings.

FIG. 1 is a perspective view of one embodiment of a heat serializable, independent dental water supply apparatus of the present invention.

FIG. 2 is a front, elevation view of the apparatus.

FIG. 3 is a side view of the apparatus.

FIG. 4 is an opposite side view of the apparatus.

FIG. 5 is a top view of the apparatus.

FIG. 6 is a bottom view of the apparatus.

FIG. 8 is a diagram of a Prior Art AQUASEPT dental water supply apparatus manufactured by Applicants' assignee, Genesis Dental Technologies of Hudson, Wis. USA, disclosed in U.S. Pat. No. 8,123,522.

FIG. 9 is a diagram of the dental water supply apparatus of FIGS. 1-7, illustrating some structural and functional distinctions relative to the Prior Art apparatus of FIG. 8.

FIG. 15 is a diagram of another embodiment of a dental system including the dental water controller of FIGS. 1-7 retrofitted with a dental hand piece and denial control unit wherein the hand piece drive is located inside the dental control unit, and wherein a foot pedal control includes a main pedal only, wherein the main foot pedal operates both hand piece drive and irrigation.

Figure 16:
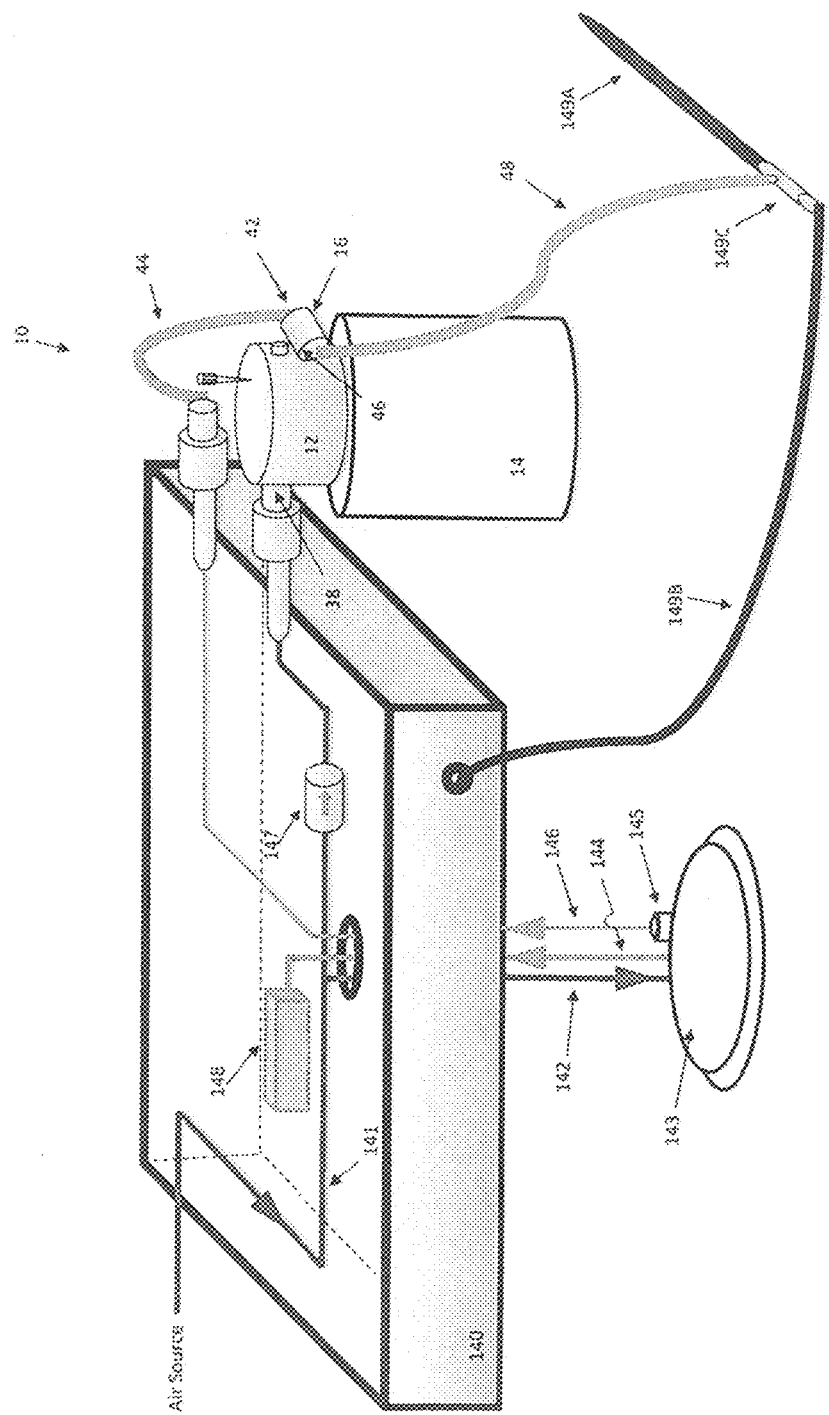

FIG. 16 is a diagram of a further embodiment of a dental system including the dental water controller of FIGS. 1-7 retrofitted with a dental hand piece and dental control unit wherein the hand piece drive is located inside the dental control unit, and wherein a foot pedal control includes both a main pedal and a chip air button, wherein, the main pedal operates the hand piece and the chip air button operates irrigation.

Figure 17:
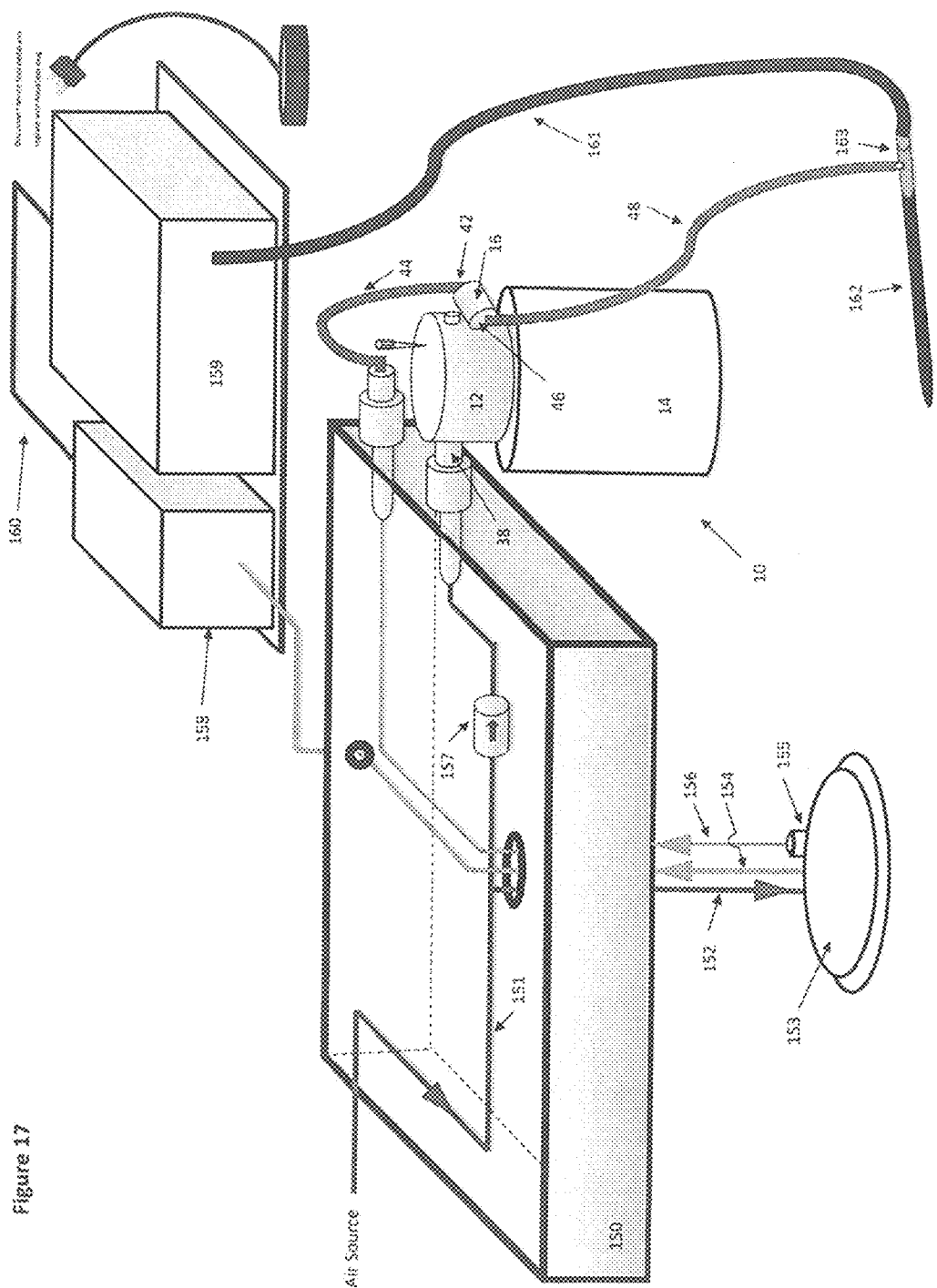

FIG. 17 is a diagram of yet another embodiment of a dental system including the dental water controller of FIGS. 1-7 retrofitted with a dental hand piece and dental control unit wherein the hand piece drive is located outside the dental control unit, and wherein a foot pedal control includes both a main pedal and a chip air button, wherein the main pedal operates the hand piece and the chip air button operates irrigation.

Figure 18:
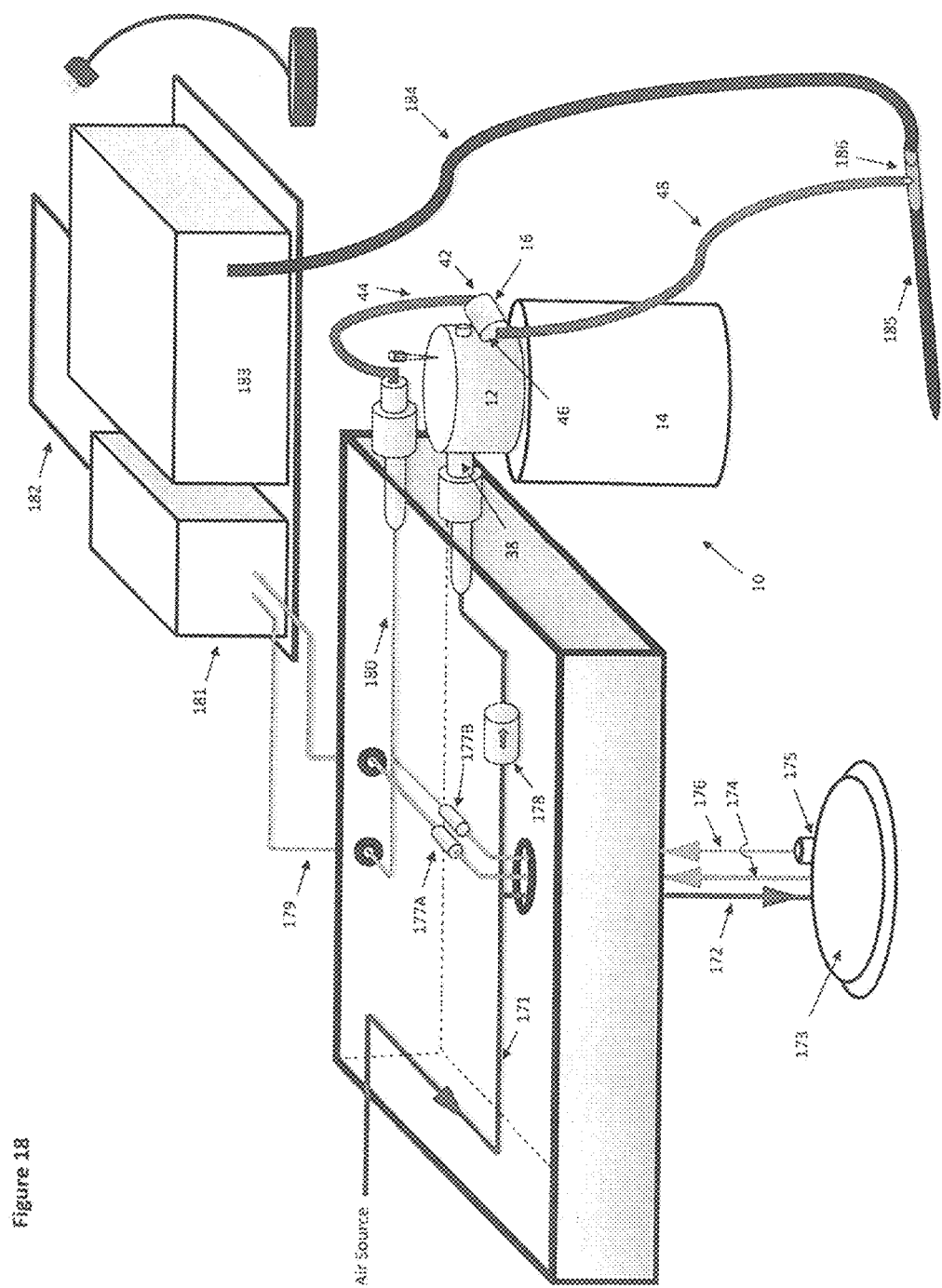

FIG. 18 is a diagram of a still further embodiment of a dental system including the dental water controller of FIGS. 1-7 retrofitted with a dental hand piece and dental control unit wherein the hand piece drive is located outside the dental control unit, and wherein a foot pedal control includes both a main pedal and a chip air button, wherein irrigation operates with the main pedal or the chip air button.

Figure 19:
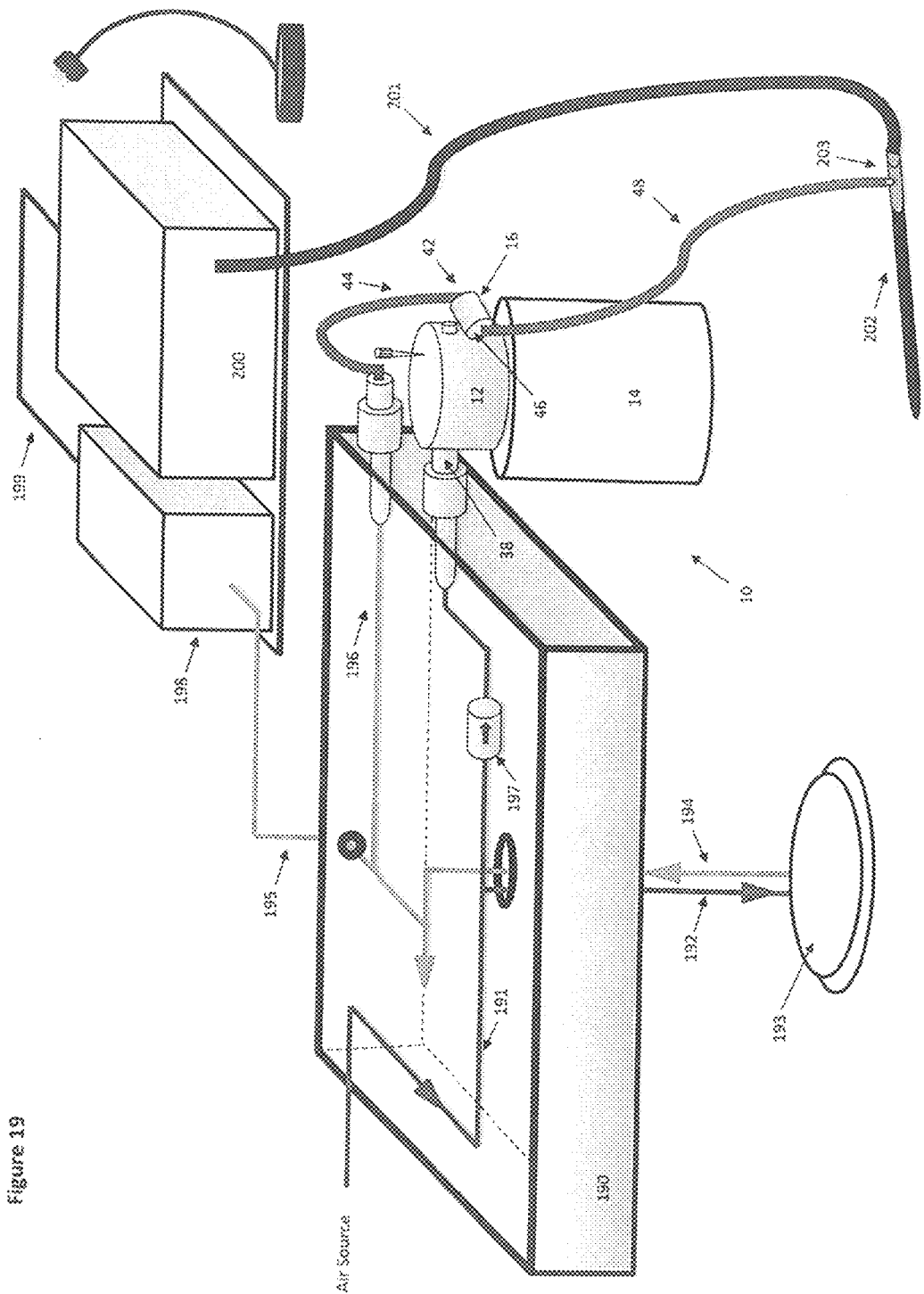

FIG. 19 is a diagram of still another embodiment of a dental system including the dental water controller of FIGS. 1-7 retrofitted with a dental hand piece and dental control unit wherein the hand piece drive is located outside the dental control unit, and wherein a foot pedal control includes a main pedal only, wherein the main foot pedal-operates both hand piece drive and irrigation.

Figure 20:
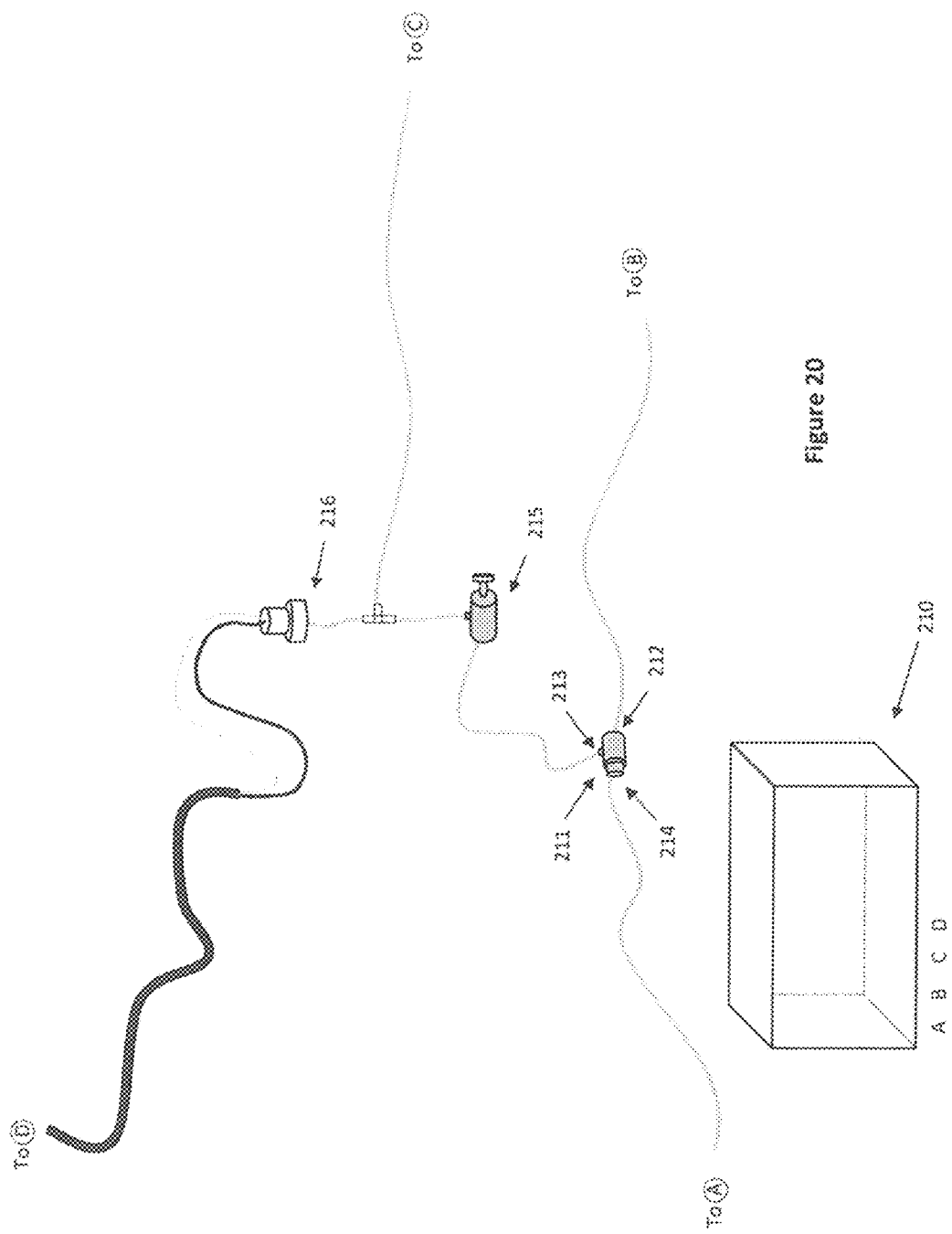

FIG. 20 is a diagram of an embodiment of a dental system including a 3 way embodiment of a dental water controller retrofitted for a dental control unit for a CAVITRON GEN-124 ultrasonic scaler hand piece.

Figure 21:
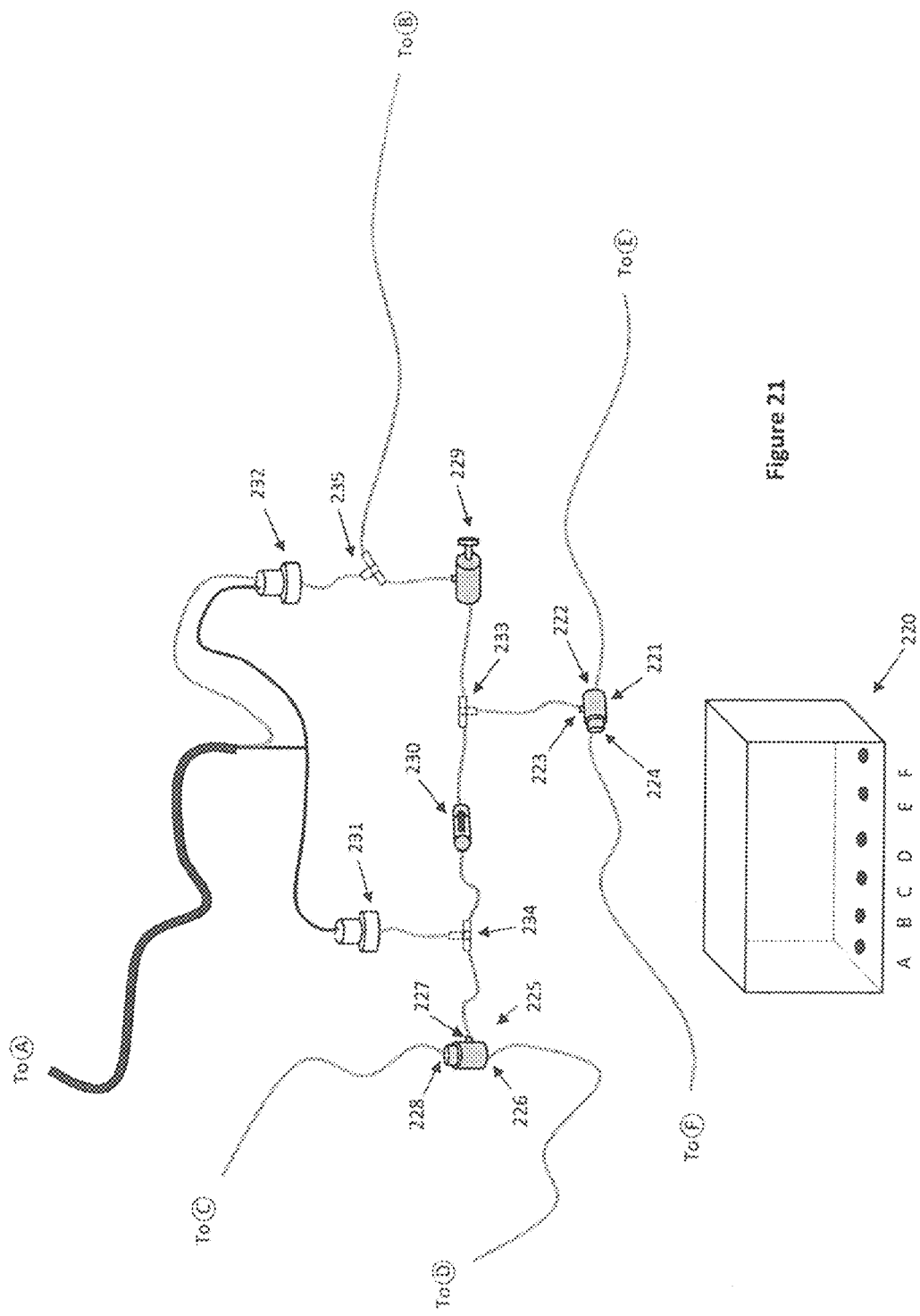

FIG. 21 is a diagram of an embodiment of a dental system including a 2 way and a 3 way embodiment of a dental water controller retrofitted for a dental control unit for a CAVITRON GEN-131 ultrasonic scaler hand piece.

Figure 22:
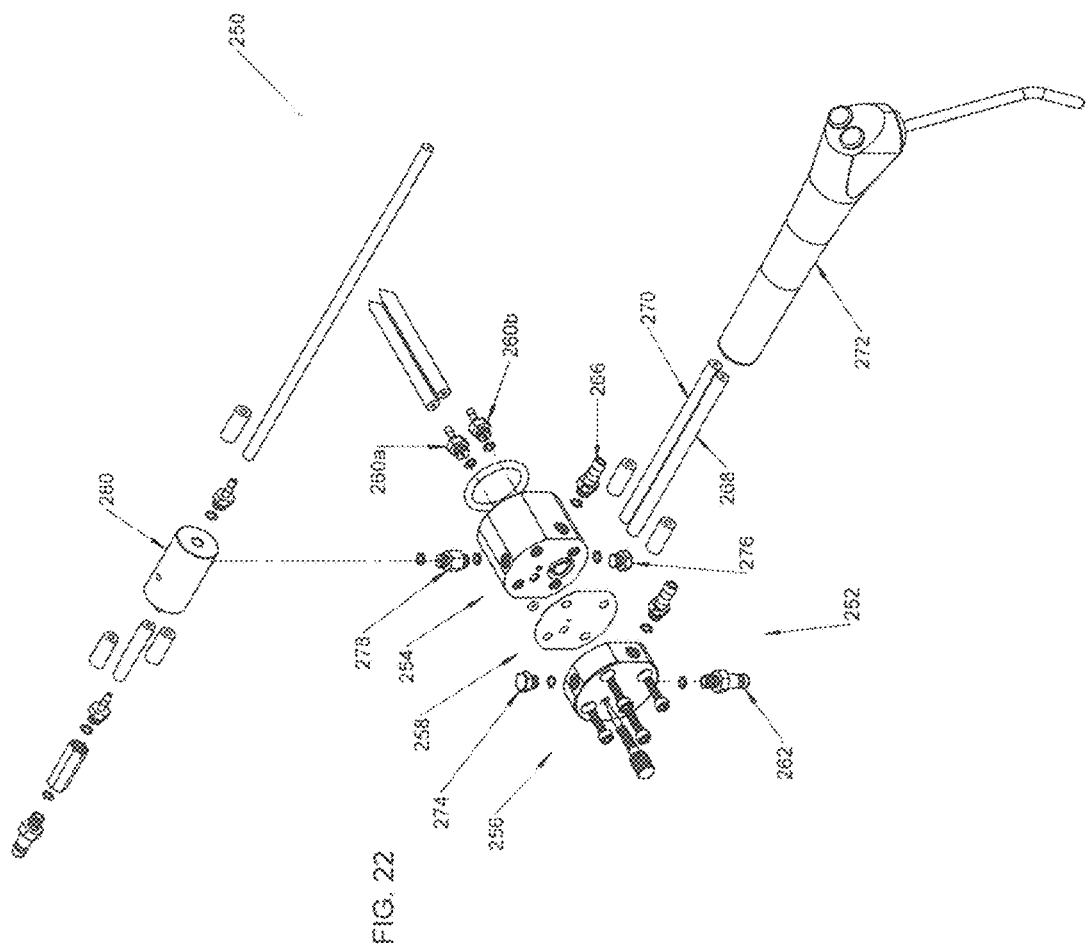

FIG. 22 is a perspective view of 2 way embodiment of the dental water supply apparatus of the present invention, including an air/water syringe therewith.

Figure 23:
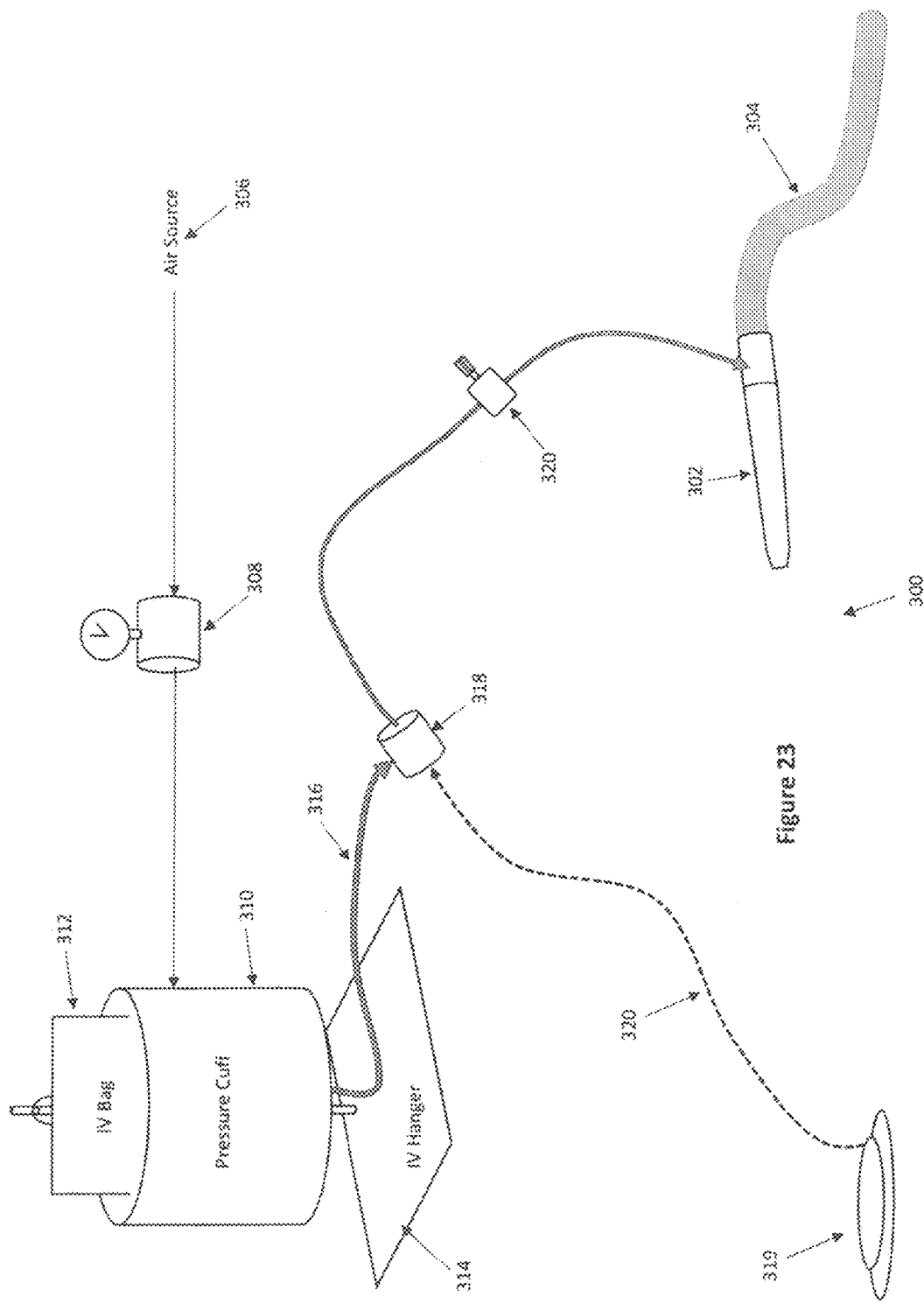

FIG. 23 is a diagram of an embodiment of a dental water control system including fluid disposed in an IV Bag type apparatus, wherein a pressure cuff pressurized the IV Bag to provide fluid flow to a dental hand piece under the control of an actuating valve (foot pedal controlled).

DETAILED DESCRIPTION

The system of the present invention optimally delivers sterile water to dental hand pieces. A prior water supply system of applicants' assignee, Genesis Dental Technologies of Hudson, Wis. USA provides sterile water only to high speed drills and air/water syringes. However, many dentists and other practitioners use surgical hand pieces other than high speed drills, for example during oral surgery. These surgical hand pieces typically utilize water as a coolant provided through a sterile IV bag and irrigation tubing. The irrigation tubing is typically connected to an irrigation nozzle disposed on the surgical hand piece.

Referring to FIGS. 1-7, a first embodiment of the heat serializable, independent dental water supply apparatus or controller 10 of the present invention comprises a hand piece control head 12, a removable water container or bottle 14 connected to the head 12 via an adapter 18, and an air activated pilot valve 16. The head 12 is constructed of a body 20, a cover 22 and a diaphragm 24 disposed between the body 20 and cover 22. The head 12 has an internal structure that is identical to the liquid coolant supply unit 51 disclosed in U.S. Pat. No. 8,123,522 to Varnes, entitled Dental Hand piece Fluid Supply Technology, which issued Feb. 28, 2012. This patent is owned by applicants' assignee, Genesis Dental Technologies (GDT), and a controller is manufactured and supplied by GDT under the mark AQUASEPT. The disclosure of the Varnes patent is hereby incorporated by reference. The liquid coolant supply unit 51 is best shown in FIGS. 4-8, and described in column 4, line 42 to column 6, line 39 of the '522 Varnes patent (hereinafter, Varnes Structures).

Figure 7:
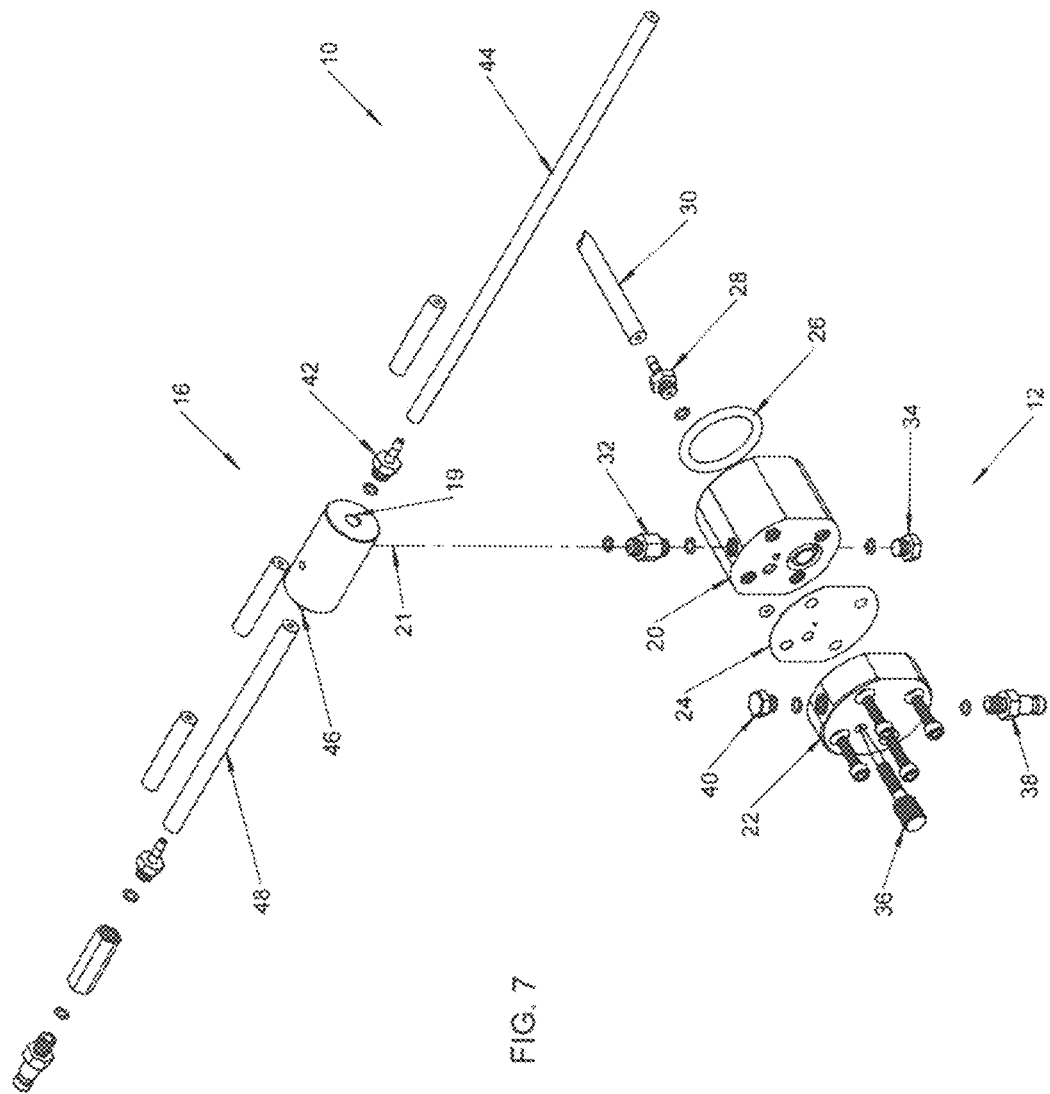
FIG. 7 is an exploded view of a portion of the apparatus.

As is best shown in FIG. 7, the body 20 has an O-ring 26 for sealing connection with the adapter 18. It is within the purview of the invention that the head 12 may be connected directly to the container 14 without the use of an adapter. A sterile water hose barb 28 extends downwardly from the body 20 for coupling to a sterile water input hose 30.

The head 12 further has a coupler 32 for connecting the air pilot valve 16, a plug 34, a needle valve 36, an air inlet fitting 38, and a plug 40. The coupler 32 is connected to and replaces the Varnes exhaust port 35. The plug 34 replaces the Varnes liquid exit fitting 31. The valve 36 is equivalent to the Varnes liquid flow adjuster screw 55. Fitting 38 replaces the Varnes gas input fitting 43. And plug 40 replaces the Varnes gas exit fitting 46.

Figure 10:
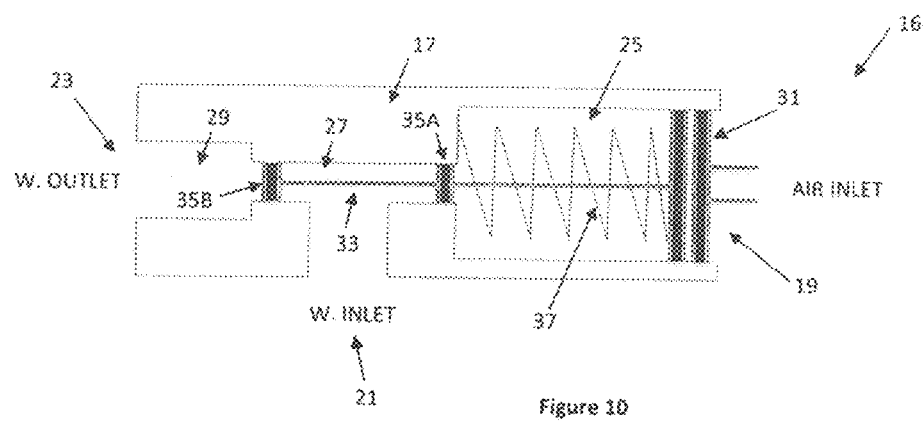
FIG. 10 is a diagram of an embodiment of an air activated pilot valve feature of the apparatus of FIGS. 1-7, in a normally closed position.
Figure 11:
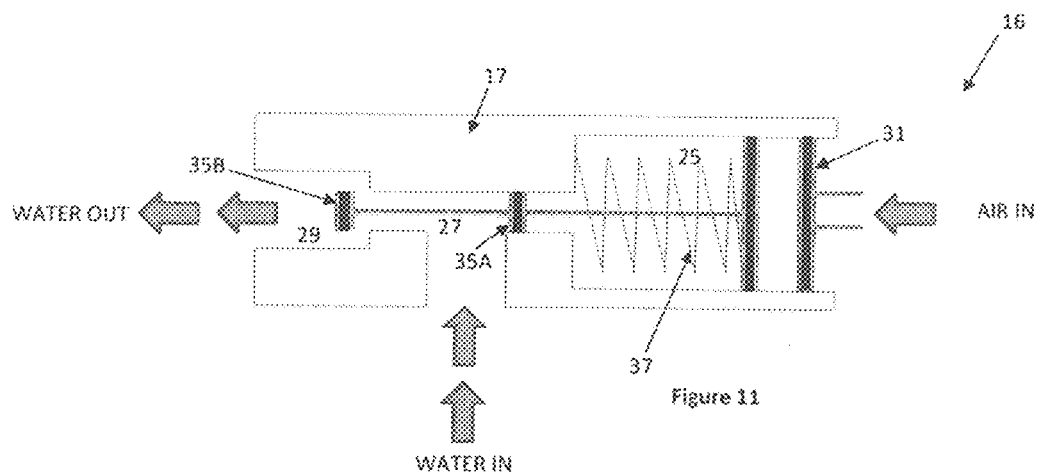
FIG. 11 is a diagram of the pilot valve of FIG. 10 in an actuated position facilitating sterile water flow to a dental hand piece.

Referring also to FIGS. 10 and 11, the air pilot valve has a cylindrical body 17 with an air inlet 19, a water inlet 21 and a water outlet 23. T lumen extends longitudinally the length of the body 17 and includes a first chamber 25, a second (middle) chamber 27 and a third chamber 29. A first, major piston 31 is removably disposed in the first chamber 25. A shaft 33 extends from the first piston 31 and is coupled to spaced apart second, minor pistons 35A and 35B, which are movably disposed in the second chamber 27. A spring 37 is disposed in the first chamber, axially with the shaft 33 and biases the first piston 31. FIG. 10 shows the air activated pilot valve 16 in its normal, closed position. FIG. 11 shows the valve 16 when actuated. Returning to FIG. 7, air inlet fitting 42 couples air hose 44 to the inlet 19. Water outlet fitting 46 couples outlet 23 to water supply hose 48.

FIGS. 8 and 9 illustrate the differences in structure and function between the Varnes—AQUASEPT controller 50 and the controller 10 of the present invention. Referring first to FIG. 8, the AQUASEPT controller 50 (Varnes 51) has a head 52, connected to sterile water supply bottle 54, and actuation pedal 56. The head 52 comprises body 60 (Varnes 20), cover 62 (Varnes 21), and diaphragm 64 (Varnes 22). Air inlet is at Point A, via connector 78 (Varnes 43) to foot pedal 56. Air Outlet is at Point B via port 80 (Varnes 46). Venting is at Point C via vent 74 (Varnes 35). Water Outlet is at Point D via port 72 (Varnes 31). And Water Inlet from bottle 54 is at tube 70 caused by pressure in Area E (Varnes 32). In a typical operation, when the foot pedal is released, air pressure is relieved at points A, B and C. This releases air pressure off of the diaphragm 64, which terminates water exiting at point D. When the foot pedal is actuated, air drives the hand piece at point B, and pressurizes bottle enclosure area E, which causes water to exit at point D.

Referring next to FIG. 9, in the hand piece control head 10 of the present invention, Air Inlet is at Point L from foot pedal 90. Port 80 is sealed at Point M by plug 40. Venting at port 74 is sealed at Point N by plug 34. Water Outlet is at Point O via the air pilot valve 16. A second Air Inlet is at Point Q via the air pilot valve 16. And the bottle 14 is pressurized at Point P. In a typical use, constant air pressure is applied at point L, which pressurizes the bottle at point P. Plugs at points M and N keep pressure on the diaphragm 24. Depressing the foot pedal 90 actuates the air pilot valve 16 at Point Q, which allows water to flow up through the tube 30, exiting at Point O. This provides an advantage over the prior art AQUASEPT device 50 because only water is supplied with full control via the foot pedal. A toggle switch can be added so that the foot pedal can still activate a hand piece, yet offer flexibility to have irrigation on or off. This is especially beneficial in the case of dental implant procedures conducted by prosthodontists and other practitioners.

Figure 12:
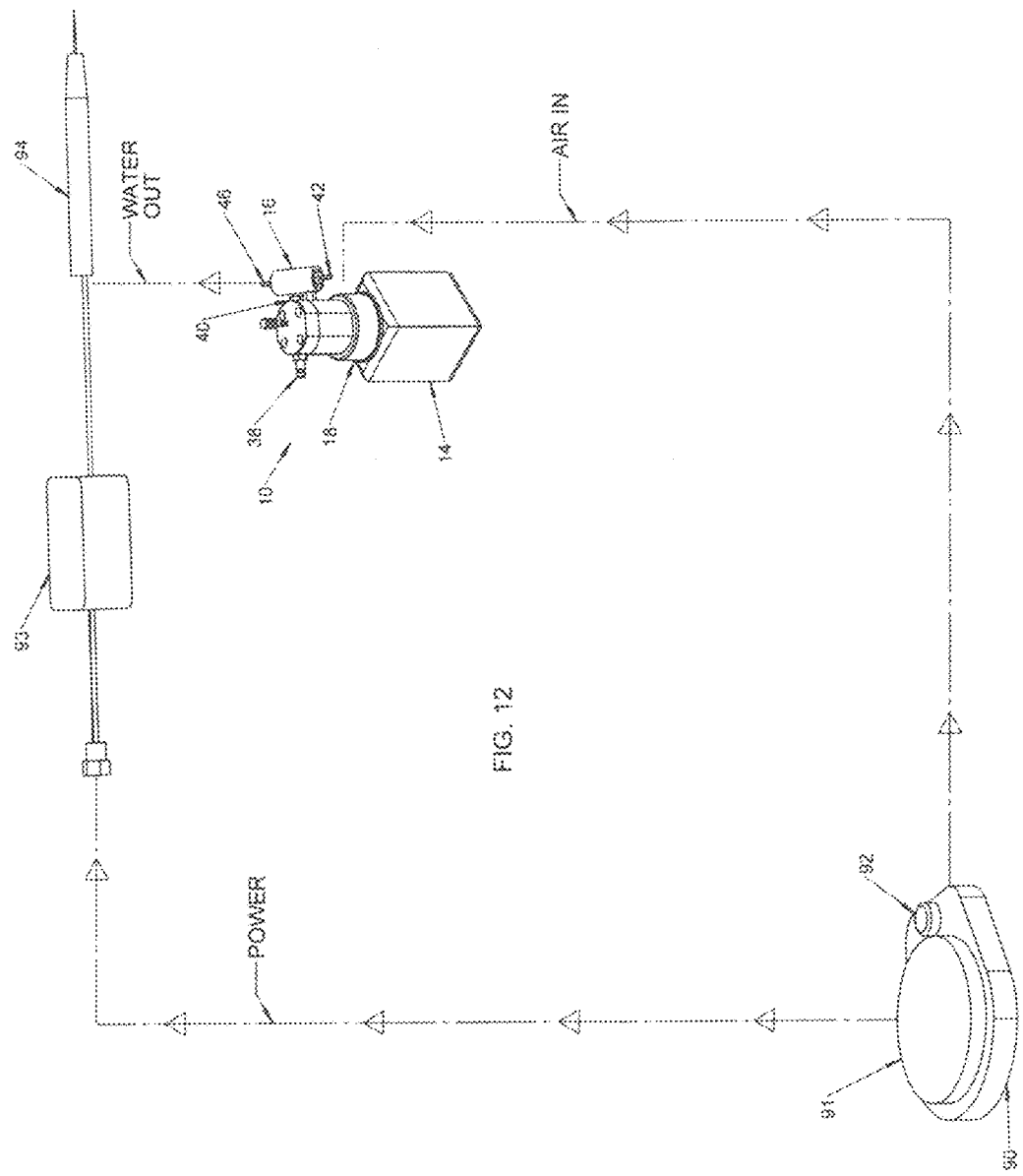
FIG. 12 is a diagram of a basic embodiment of a denial water supply system including dental water controller of FIGS. 1-7 with a conventional air or electric powered dental hand piece including a drill and drive system therefor.

FIG. 12 illustrates a common connection of the dental water supply apparatus 10 deployed with a conventional electric or other hand piece 94 to provide on/off flexibility. Foot pedal 90 includes a main pedal 91 that turns the hand piece on and off. Foot pedal 90 also includes a chip air button 92 which turns irrigation on and off. Foot pedal is connected to hand piece drive box 93, which is communicatively connected to the hand piece 94. Foot pedal 90 is also connected to the dental water supply apparatus 10, which has a water line connection to the hand piece 94.

Figure 13:
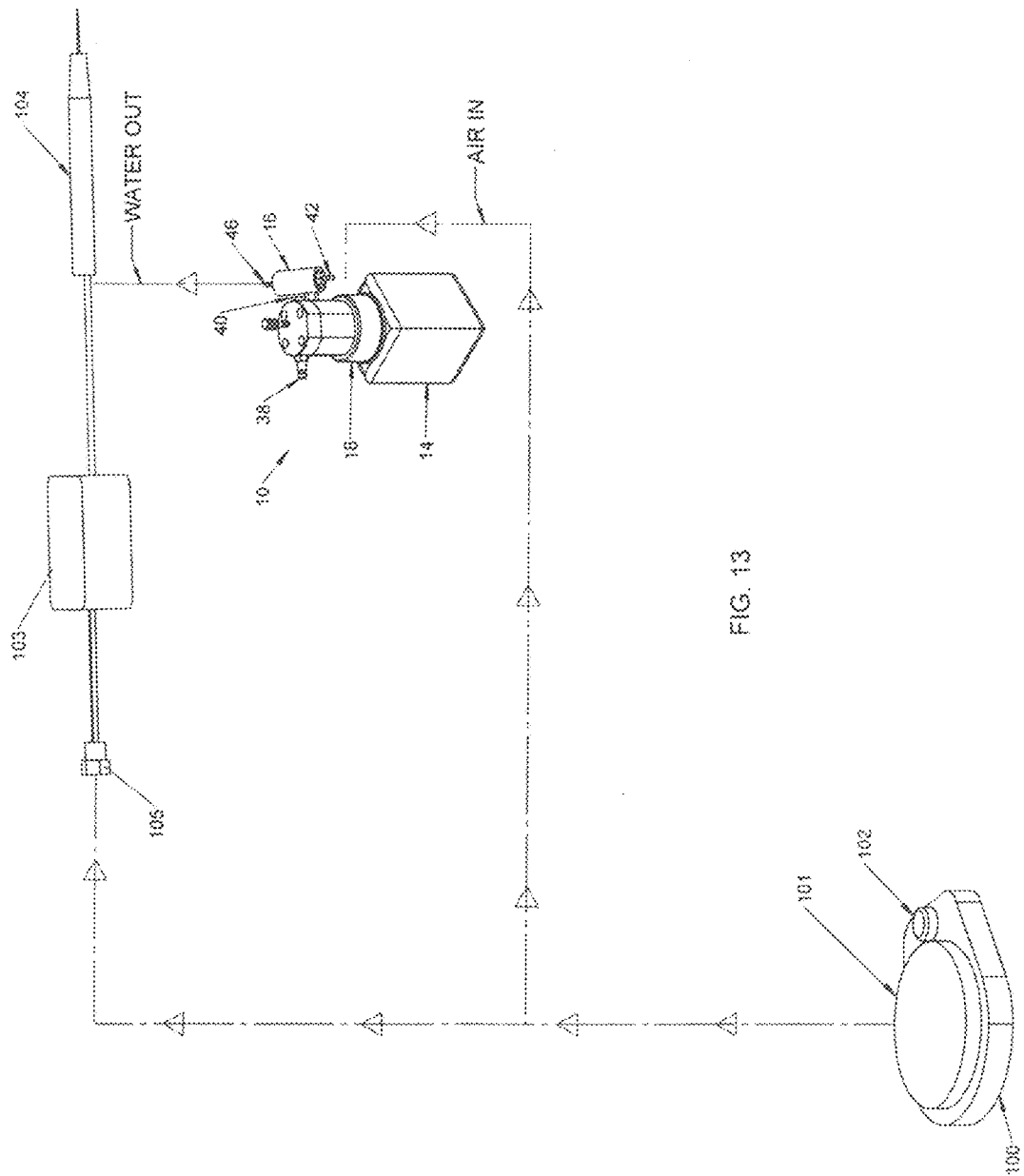
FIG. 13 is a diagram of another basic embodiment of a dental water supply system including dental water controller of FIGS. 1-7 with an ultrasonic scaling hand piece and drive system therefor.

FIG. 13 illustrates a common connection of the dental water supply apparatus 10 deployed with an ultrasonic hand piece 104 such as a CAVITRON scaler. Devices of this type require continuous water supply. Foot pedal 100 includes a main pedal 101 that turns the hand piece 104 on and off. Foot pedal 100 also includes a chip air button 102 which turns irrigation on and off. Foot pedal 100 is connected to ultrasonic scaling unit, via air/electric switch 105, which is communicatively connected to the ultrasonic scaler 104. Foot pedal 100 is also connected to the dental water supply apparatus 10, which has a water line connection to the hand piece 104.

Figure 14:
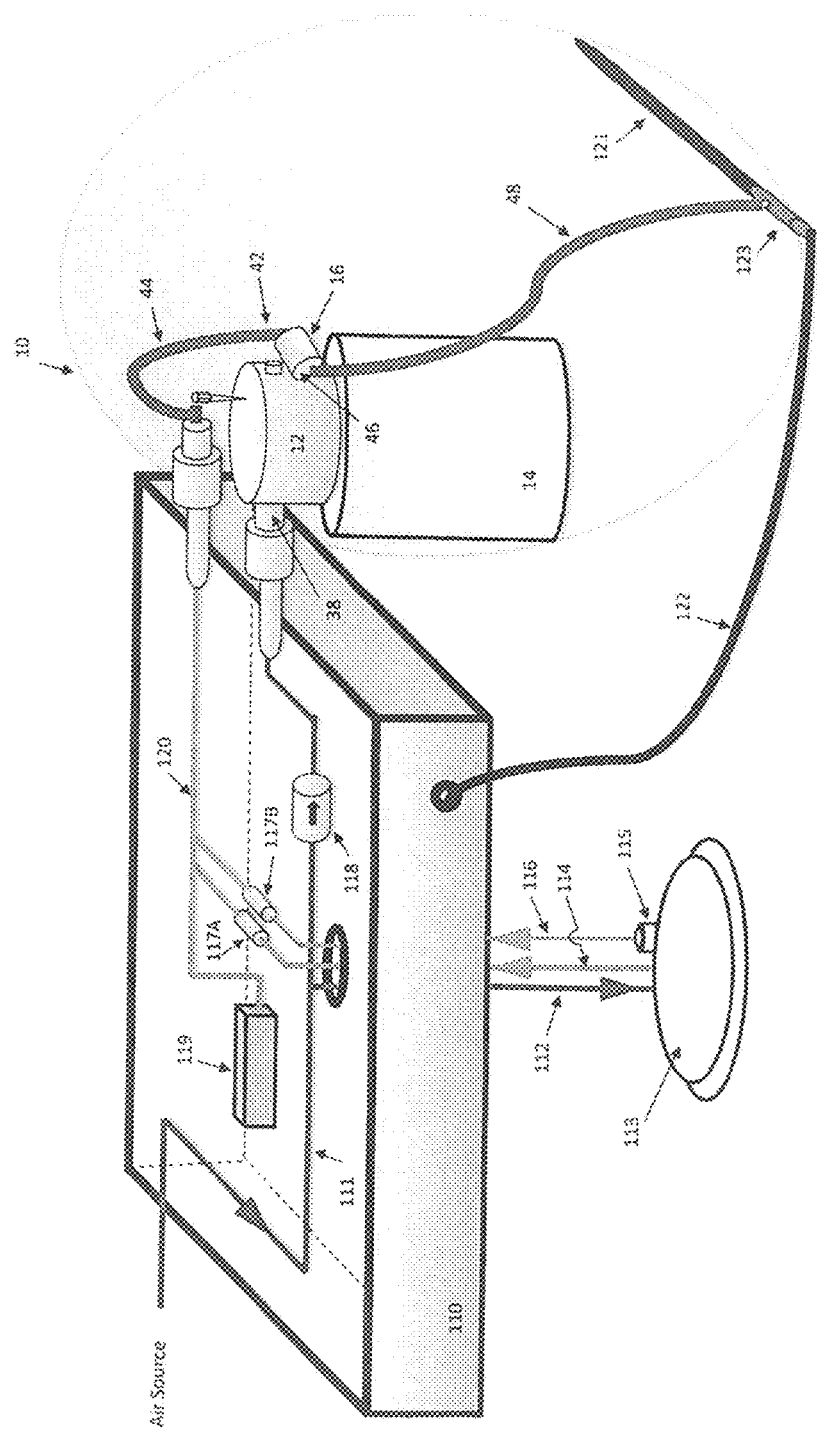
FIG. 14 is a diagram of an embodiment of a dental system including the dental water controller of FIGS. 1-7 retrofitted with a dental hand piece and dental control unit wherein the hand piece drive is located inside the dental control unit, and wherein a foot pedal control includes both a main pedal and a chip air button, wherein irrigation operates with the main pedal or the chip air button.

FIG. 14 is a diagram of an embodiment of a dental system including the dental water controller 10 of FIGS. 1-7 and 9 retrofitted with a dental hand piece 121 and dental control unit 110 wherein the hand piece drive 119 is located inside the dental control unit 110, and wherein a foot pedal control includes both a main pedal 113 and a chip air button 115, wherein irrigation is provided by the main pedal 113 or the chip air button 115. A main air source provides air via line 111 to the hand piece control head 12 at air inlet 38 via inline regulator 118, for example at approximately 35 psi. Device motor 119 is connected to the hand piece 121 via line 122 and also to the air inlet 42 of the air pilot valve 116 via line 120. The water outlet 46 is connected to the hand piece 121 via line 48 to adapter 123. Foot pedal is connected to the air source via connected line 112. Pedal 113 air and chip air 115 are connected to the air pilot valve 16 via lines 114 and 116 respectively through respective check valves 117A and B. Elements shown in the shaded blue area are components that may be easily sterilized between procedures, ensuring safe, sterile delivery of irrigant to all patients.

Figure 15:
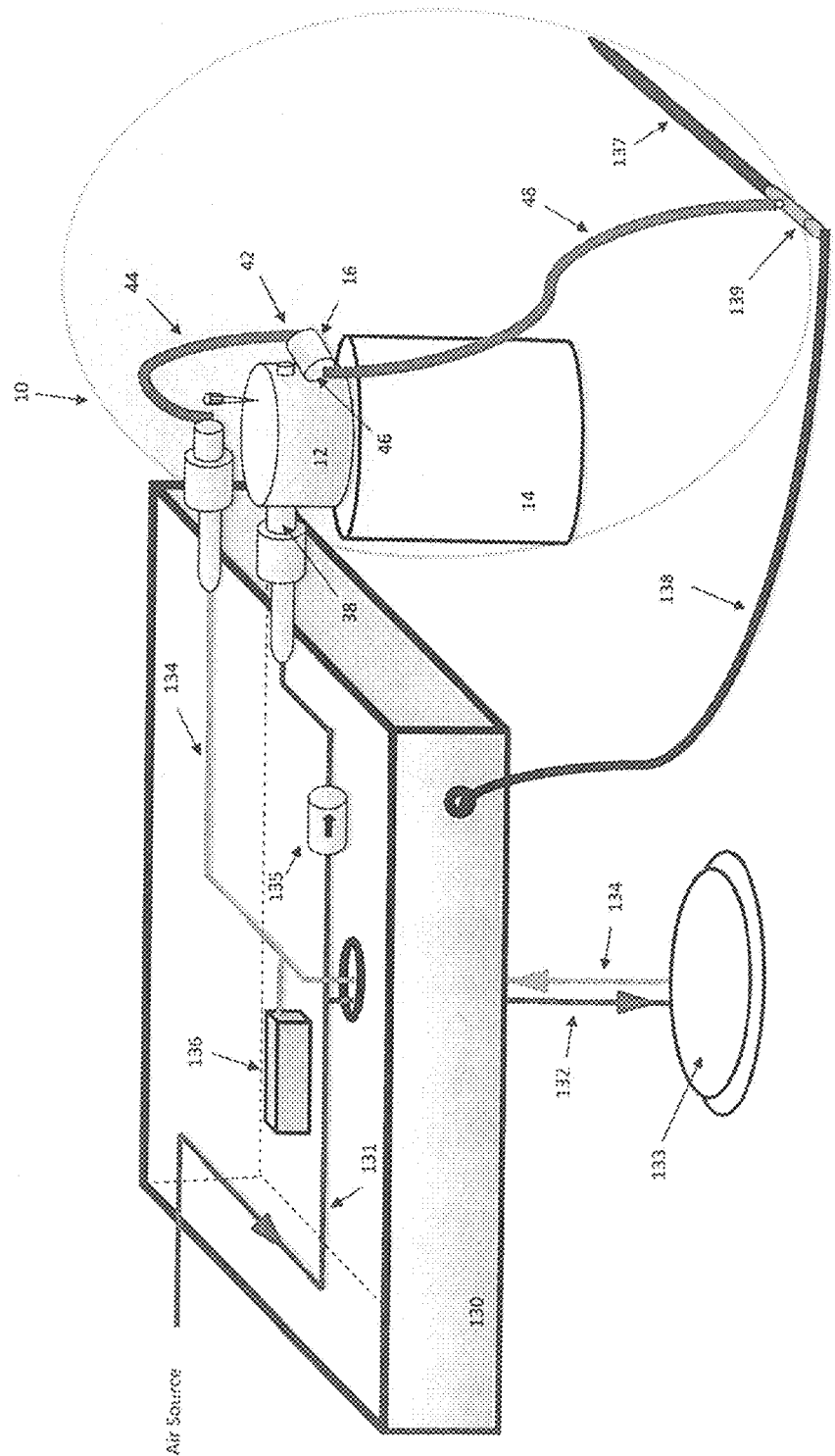

FIG. 15 is a diagram of another embodiment of a dental system including the dental water controller 10 retrofitted with a dental hand piece 137 and dental control unit 130 wherein the hand piece drive 136 is located inside the dental control unit 130, and wherein a foot pedal control includes a main pedal 133 only, wherein the main foot pedal 133 operates both hand piece 137 drive and irrigation. A main air source provides air via line 131 to the hand piece control head 12 at air inlet 38 via inline regulator 135, for example at approximately 35 psi. Device motor 136 is connected to the hand piece 137 via line 134 and also to the air inlet 42 of the air pilot valve 116. The water outlet 46 is connected to the hand piece 137 via line 48 to adapter 139. Foot pedal 133 is connected to the air source via connected line 132. Pedal 133 air is connected to the air pilot valve 16 via line 134.

FIG. 16 is a diagram of a further embodiment of a dental system including the dental water controller 10 retrofitted with a dental handpiece 149 and dental control unit 140 wherein the hand piece drive 148 is located inside the dental control unit 140, and wherein a toot pedal control includes both a main pedal 143 and a chip air button 145, wherein the main pedal 143 operates the hand piece 149A and the chip air button 145 operates irrigation. A main air source provides air via line 141 to the hand piece control bead 12 at air inlet 38 via inline regulator 147, for example at approximately 35 psi. Device motor 148 is connected to the hand piece 149A via line 149B and also to the foot pedal via line 144. The water outlet 46 is connected to the hand piece 149A via line 48 to adapter 149C. Foot pedal is connected to the air source via connected line 142. Chip air 145 is connected to the air pilot valve 16 via line 146.

FIG. 17 is a diagram of yet another embodiment of a dental system including the dental water controller 10 retrofitted with a dental hand piece 162 and dental control unit 150 wherein the hand piece drive 159 is located outside the dental control unit 150, and wherein a foot pedal control includes both a main pedal 153 and a chip air button 155, wherein the main pedal 153 operates the hand piece 162 and the chip air button 155 operates irrigation. A main air source provides air via line 151 to the hand piece control head 12 at air inlet 38 via inline regulator 157, for example at approximately 35 psi. Device motor 159 is connected to the hand piece 162 via line 161. The water outlet 46 is connected to the hand piece 162 via line 48 to adapter 163. Foot pedal is connected to the air source via connected line 152. Pedal 153 air is connected to the external device drive 159 via a loot pedal retrofit kit 158 and cable 160. Chip air 155 is connected to the air pilot valve 16 via line 156.

FIG. 18 is a diagram of a still further embodiment of a dental system including the dental water controller 10 retrofitted with a dental hand piece 185 and dental control unit 170 wherein the hand piece drive 183 is located outside the dental control unit 170, and wherein a foot pedal control includes both a main pedal 173 and a chip air button 175, wherein irrigation operates with the main pedal 173 or the chip air button 175. A main air source provides air via line 171 to the hand piece control head 12 at air inlet 38 via inline regulator 178, for example at approximately 35 psi. External device motor 183 is connected to the hand piece 185 via line 184. The water outlet 46 is connected to the hand piece 1185 via line 48 to adapter 186. Foot pedal is connected to the air source via connected line 172. Pedal 113 air is connected to the drive 185 via retrofit kit 181 (and cable 182) by line 174 through check valve 177A. Chip air 175 is also to the retrofit kit 181 via line 176 (through cheek valve 177B), which is also connected to the air pilot valve 16 via line 180.

FIG. 19 is a diagram of still another embodiment of a dental system including the dental water controller 10 retrofitted with, a dental hand piece 202 and dental control unit 190 wherein the hand piece drive 200 is located outside the dental control unit 190, and wherein a foot pedal control includes a main pedal 193 only, wherein the main foot pedal 193 operates both hand piece 202 drive and irrigation. A main air source provides air via line 1191 to the hand piece control head 12 at air inlet 38 via inline regulator 197, for example at approximately 35 psi. External device motor 200 is connected to the hand piece 1202 via line 201. The water outlet 46 is connected to the hand piece 202 via line 48 to adapter 203. Foot pedal 193 is connected to the air source via connected line 192. Pedal 193 air is connected, via line 194, to the driver 200 through retrofit kit 198 (and cable 199), and further via line 196 to the air pilot valve 16.

The water supply apparatus 10 will also work in conjunction with an ultrasonic device such as a scaler. Other adaptations of the device may permit operation of a piezo, electric motor (or any device that utilizes an on/off foot pedal), that is separate (or built into) a dental unit and improve performance with the existing dental unit foot pedal. This permits a dentist to utilize their equipment by eliminating the apparatus foot pedal. By doing this, the system is act vatable simultaneously. This permits provision of water to the apparatus hand piece simultaneously. Thereby, the journey of water from the source to the hand piece is seamless. An end result is that the dentist is able to utilize their equipment and provide full water control with Aqua Sept without any perceivable limitation. FIG. 20 is a diagram of an embodiment of a dental system including a 3 way embodiment of a dental water controller retrofitted for a dental control unit for a CAVITRON GEN-124 ultrasonic sealer hand piece. Control box 210 has a Toggle (chip air) connection A, a foot pedal connection B, a connection for the water supply apparatus 10 C, and a Cavitron connection D. Interconnected components by the lines and destinations include a two way-controller 211 (input 212, output 213, and actuator 214), an adjustable regulator 215, and air/electric switch 216. FIG. 21 is a diagram of an embodiment of a dental system including a 2 way and a 3 way embodiment of a dental water controller retrofitted for a dental control unit for a CAVITRON GEN-131 ultrasonic scaler hand piece. Control box 220 has a Cavitron connection A, a water supply 10 connection B, a boost connection C, and a main air connection D, and a toggle connection E. Interconnected components by the lines and destinations include a 2 way air pilot device 221 (input 222, output 223, actuator 224), a 3 way air pilot mechanism 225 (input 226, output 227, and actuation 228), an adjustable regulator 229, a check valve 230, switches 231 and 232 and T connections 233, 234 and 235.

FIG. 22 is a perspective view of 2 way embodiment of the dental water supply apparatus of the present invention, including an air/water syringe therewith. The apparatus 250 has a head 25 with a body 254, cover 256 and diaphragm 258, and a hand piece 272. The head 25 further comprises connector barbs 260A/B, air in fitting 262, hand piece fittings 264 and 266, hoses 268 and 270, plugs 274 and 276, and connector 268.

Referring to FIG. 23, an embodiment of the system which utilizes an IV bag or the like for a sterile water source is shown. This embodiment of the system has a direct source air line and a regulator. An autoclavable valve is disposed before the point where the IV line goes into the hand piece adapter. This permits regulation of the flow of irrigant to the hand piece. And, an air pilot valve is disposed before the valve. The air pilot receives air from the foot pedal (chip air and regular air) which turns on and off the flow of irrigant to the hand piece. The system 300 includes a hand piece 302 with drive line 304, an air source 306 connected to a pressure cuff 310 through a regulator 308, an IV bag 312 disposed in the cuff 310 and hung by hanger 314. IV line 316 runs to actuator 318 which is connected to pedal 319, and then to the hand piece 302 through flow control device 320.

The system of the present invention replaces the prior art IV bag and tube system used by oral surgeons and other specialist dental practitioners. The system can apply to any hand piece that has an autoclavable adapter for disposable tubing to attach, i.e. ultrasonic scaling, implant drills, etc. The system provides foot pedal control and fluid volume control. The system permits retrofitting dental unit with a simple to use sterile delivery for all hand pieces is now available. In contrast, the prior IV bag system with peristaltic pump is cumbersome, requires maintenance, and limited space is available for the pump.

All components are autoclavable. To achieve this, the system is compact and detachable. The system works by utilizing air to pressurize a water bottle and run hand piece at the same time. To run a high speed drill, a diaphragm is pressurized causing a water reservoir to fill, allowing a controlled level (needle valve) of water to discharge through a barb. The air merely passes over this diaphragm to keep pressure applied, and is exited through a barb to run a hand piece.

By replacing the IV bag system the practitioner has more control of sterile irrigation. The has full control of an electric hand piece and is able to turn on and off irrigation utilizing the chip air function of their foot pedal. For the first time ever, the doctor can now run a hand piece without requiring an assistant to control the irrigation. The doctor now has foil control of when and how much irrigation for each procedure. And, the entire system can be autoclaved between patients, allowing for sterile delivery.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. A dental water supply apparatus for use with a dental hand piece, comprising
a hand piece control head adapted to be connectible to an air supply, an actuator, and a dental hand piece, the control head including an air actuated pilot valve, the pilot valve including:
a body with a central lumen extending from a first end to an opposing second end, an air at the first end, a water inlet disposed along the length of the central lumen, and a water outlet disposed at the second end,
a valve assembly including a major piston actuable by inlet air, a shaft extending from the major piston to two minor pistons disposed between the water inlet and the water outlet;
whereby the major piston is spring biased in a normally closed position the minor pistons prevents flow of water from the water inlet to the water outlet; and whereby inlet air actuation of the major piston causes it to be in an open position permitting flow of water from the water inlet to the water outlet;

wherein the lumen has a first chamber in which the major piston is movably disposed, a second chamber extending from the first chamber and being communicatively connected with the water inlet, and a third chamber extending from the second chamber to the water outlet;

a spring is disposed in the first chamber behind the major piston; and the two minor pistons disposed on the shaft, one disposed between the first and second chambers and the other disposed between the second and third chambers;

a removable water supply container, the container supplying water to the hand piece control head; and the hand piece control head being directly connectible to and disconnectible from the water supply container.

2. The dental water supply apparatus of claim 1, wherein the hand piece control head is constructed of autoclavable materials.

3. The dental water supply apparatus of claim 1, wherein the hand piece control head includes a body that is directly connectible to the water supply container via a threaded adapter portion of the body, a diaphragm disposed on the body on a side opposite that of the threaded adapter portion, a cover, disposed on the diaphragm, and wherein the pilot valve is connected to the body.

4. The dental water supply apparatus of claim 3, wherein the cover is adapted to be connected to an air supply, wherein the pilot valve is adapted to be connected to an air supply of an actuator, and wherein the body receives water from the container and distributes it to the pilot valve for transmission to the hand piece.

5. The dental water supply apparatus of claim 1, further comprising the actuator and the dental handpiece.

6. The dental water supply apparatus of claim 5, further comprising the air supply.

7. The dental water supply apparatus of claim 5 further comprising a hand piece drive mechanism.

8. The dental water supply apparatus of claim 1, wherein the control head has a threaded adapter, wherein the water supply container has a threaded adapter, and wherein the threaded adapter of the control head screws onto and off of the threaded adapter of the water supply container directly connecting and disconnecting the control head to and from the water supply container.

9. The dental water supply apparatus of claim 8, wherein the control head threaded adapter is a female type adapter and the water supply container threaded adapter is a male type adapter.

10. A dental water supply apparatus for use with a dental hand piece, comprising a. a hand piece control head adapted to be connectible to an air supply, an actuator, and a dental hand piece, the control bead including an air actuated pilot valve, the pilot valve including:

a body with a central lumen extending from a first end to an opposing second end, an air inlet at the first end, a water inlet disposed along the length of the central lumen, and a water outlet disposed at the second end, valve assembly including a major position actuatable by inlet air, a shaft extending from the major piston to two minor pistons disposed between the water inlet and the water outlet;

whereby the major is spring biased in a normally closed position wherein the minor pistons prevents flow of water from the water inlet to the water outlet; and whereby inlet air actuation of the major piston causes it to be in an open position permitting flow of water from the water inlet to the water outlet;

wherein:

the central lumen has a first chamber in which the major piston is movably disposed, a second chamber extending from the first chamber and being communicatively connected with the water inlet, and a third chamber extending g from the second chamber to the water outlet;

a spring is disposed in the first chamber behind the major piston; and the two minor pistons disposed on the shaft, one disposed between the first and second chambers and the other disposed between the second and third chambers;

b. a removable water supply container, the container supplying water to the hand piece control head;

c. wherein the hand piece control head is directly connectible to and disconnectible from the water supply container;

d. wherein the control head has a threaded adapter, wherein the water supply container has a threaded adapter, and wherein the threaded adapter of the control head screws onto and off of the threaded adapter of the water supply container directly connecting and disconnecting the control head to and from the water supply container; and e. wherein a cover is adapted to be connected to an air supply, wherein the pilot valve is adapted to be connected to an air supply of an actuator, and wherein the body receives water from the container and distributes it to the pilot valve for transmission to the hand piece.

11. A dental water supply apparatus for use with a dental hand piece, comprising a. a hand piece control head adapted to be connectible to an air supply, an actuator, and a dental hand piece, the control head including an air actuated pilot valve; and b. a removable water supply container, the container supplying water to the hand piece control head;

c. wherein the hand piece control head is directly connectible to and disconnectible from the water supply container;

d. wherein the control head has a threaded adapter, wherein the water supply container has a threaded adapter, and wherein the threaded adapter of the control head screws onto and off of the threaded adapter of the water supply container directly connecting and disconnecting the control head to and from the water supply container, e. wherein a cover is adapted to be connected to an air supply, wherein the pilot valve is adapted to be connected to an air supply of an actuator, and wherein the body receives water from the container and distributes it to the pilot valve for transmission to the hand piece; and f. wherein the pilot valve comprises:

(i) a body with a central lumen extending from a first end to an opposing second end, an air inlet at the first end, a water inlet disposed along the length of the central lumen, and a water outlet disposed at the second end, (ii) a valve assembly including a major piston actuatable by inlet air, a shaft extending from the major piston to two minor pistons disposed between the water inlet and the water outlet;
(iii) whereby the major piston is spring biased in a normally closed position wherein the minor pistons prevents flow of water from the water inlet to the water outlet; and
(iv) whereby inlet air actuation of the major piston causes it to be in an open position permitting flow of water from the water inlet to the water outlet, and
(v) wherein:
   the central lumen has a first chamber in which the major piston is movably disposed, a second chamber extending from the first chamber and being communicatively connected with the inlet, and a third chamber extending from the second chamber to the water outlet;
   a spring is disposed in the first chamber behind the major piston; and
   the two minor pistons disposed the shaft, one disposed between the first and second chambers and the other disposed between the second and third chambers.

* * * * *